US00PP30336P2

(12) United States Plant Patent
Koppe

(10) Patent No.: US PP30,336 P2
(45) Date of Patent: Apr. 2, 2019

(54) ***BEGONIA* PLANT NAMED 'KRBEVPE02'**

(50) Latin Name: ***Begonia* x *hiemalis***
Varietal Denomination: KRBEVPE02

(71) Applicant: Lubbertus H. Koppe, Putten (NL)

(72) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 0 days.

(21) Appl. No.: 15/732,404

(22) Filed: Nov. 6, 2017

(51) Int. Cl.
*A01H 5/02* (2018.01)

(52) U.S. Cl.
USPC ..... Plt./347

(58) Field of Classification Search
USPC ..... Plt./344, 347
See application file for complete search history.

*Primary Examiner* — Susan McCormick Ewoldt
(74) *Attorney, Agent, or Firm* — C. A. Whealy

(57) ABSTRACT

A new and distinct cultivar of *Begonia* plant named 'KRBEVPE02' characterized by its upright to outwardly spreading and mounded plant habit; moderately vigorous growth habit; freely flowering habit; semi-double type flowers that are light orange and light red in color and held above and beyond the foliar plane; and excellent postproduction longevity.

2 Drawing Sheets

Botanical designation: *Begonia* x *hiemalis*.
Cultivar denomination: 'KRBEVPE02'.

BACKGROUND OF THE INVENTION

The present invention relates to a new and distinct cultivar of *Begonia* plant, botanically known as *Begonia* x *hiemalis*, commercially referred to as an Elatior *Begonia* and hereinafter referred to by the name 'KRBEVPE02'.

The new *Begonia* plant is a product of a planned breeding program conducted by the Inventor in Ermelo, The Netherlands. The objective of the breeding program is to create new vigorous *Begonia* plants with excellent postproduction longevity and attractive flower color.

The new *Begonia* plant originated from a cross-pollination made by the Inventor in Ermelo, The Netherlands in January, 2013 of a proprietary selection of *Begonia* x *tuberhybrida* hybrid identified as code number KV11K1933-011, not patented, as the female, or seed, parent with a proprietary selection of *Begonia socotrana* identified as code number S00, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in January, 2014. Asexual reproduction of the new *Begonia* plant by terminal vegetative cuttings taken in a controlled greenhouse environment in Ermelo, The Netherlands since April, 2014 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRBEVPE02'. These characteristics in combination distinguish 'KRBEVPE02' as a new and distinct *Begonia* plant:

1. Upright to outwardly spreading and mounded plant habit.
2. Moderately vigorous growth habit.
3. Freely flowering habit.
4. Semi-double type flowers that are light orange and light red in color and held above and beyond the foliar plane.
5. Excellent postproduction longevity.

Plants of the new *Begonia* differ primarily from plants of the female parent selection in flower color as plants of the female parent selection have yellow-colored flowers.

Plants of the new *Begonia* differ primarily from plants of the male parent selection in flower color as plants of the male parent selection have light red purple-colored flowers. In addition, plants of the *Begonia* have semi-double type flowers whereas plants of the male parent selection have single type flowers.

Plants of the new *Begonia* can be compared to plants of *Begonia* x *hiemalis* 'Dark Britt', not patented. In side-by-side comparisons conducted in Ermelo, The Netherlands, plants of the new *Begonia* differ primarily from plants of 'Dark Britt' in flower type as plants of 'Dark Britt' have more fully double type flowers. In addition, plants of the new *Begonia* have larger flowers than plants of 'Dark Britt'.

Plants of the new *Begonia* can also be compared to plants of *Begonia* x *hiemalis* 'KRELECE01', disclosed in U.S. Plant Pat. No. 28,187. In side-by-side comparisons conducted in Ermelo, The Netherlands, plants of the new *Begonia* differ primarily from plants of 'KRELECE01' in flower type as plants of 'KRELECE01' have fully double type flowers. In addition, plants of the new *Begonia* and 'KRELECE01' differ in flower color as plants of 'KRELECE01' have cerise-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical plant of 'KRBEVPE02' grown in a container.

The photograph on the second sheet are close up views of the upper (right) and lower (left) surfaces of typical leaves and flowers of 'KRBEVPE02', and in the center of the photograph is a close-up view of typical flower buds.

DETAILED BOTANICAL DESCRIPTION

The aforementioned photographs and following observations and measurements describe plants grown during the late spring and early summer in 12-cm containers in a glass-covered greenhouse in Ermelo, The Netherlands and under cultural practices typical of commercial *Begonia* production. During the production of the plants, day temperatures averaged 20° C. and night temperatures averaged 18° C. Plants were three months old when the photographs and description were taken. In the following description, color references are made to The Royal Horticultural Society Colour Chart, 2015 Edition, except where general terms of ordinary dictionary significance are used.

Botanical classification: *Begonia* x *hiemalis* 'KRBEVPE02'.

Parentage:

*Female, or seed, parent*.—Proprietary selection of *Begonia* x *tuberhybrida* hybrid identified as code number KV11K1933-011, not patented.

*Male, or pollen, parent*.—Proprietary selection of *Begonia socotrana* identified as code number S00, not patented.

Propagation:

*Type*.—By terminal vegetative cuttings.

*Time to initiate roots, summer and winter*.—About 20 days at temperatures about 20° C.

*Time to produce a rooted young plant, summer and winter*.—About five weeks at temperatures about 20° C.

*Root description*.—Fine, fibrous; typically white to orange brown in color, actual color of the roots is dependent on substrate composition, water quality, fertilizer type and formulation, substrate temperature and physiological age of roots.

*Rooting habit*.—Freely branching; medium density; plants of the new *Begonia* have not been observed to form tubers.

Plant description:

*Plant habit and form*.—Upright to outwardly spreading and mounded plant habit; overall plant shape, broadly obovate to globular.

*Growth habit*.—Moderately vigorous growth habit and moderate to rapid growth rate; suitable for 12-cm and larger containers; under optimal environmental and cultural conditions, usually about nine weeks are required to produce proportional plants in 12-cm containers.

*Branching habit*.—Moderately freely branching with about four primary branches developing per plant.

*Plant height, soil level to top of foliar plane*.—About 32.1 cm.

*Plant height, soil level to top of floral plane*.—About 35.5 cm.

*Plant width*.—About 46.8 cm.

*Lateral branches*.—Length: About 16.3 cm. Diameter: About 0.9 cm to 1.1 cm. Internode length: About 4.4 cm. Strength: Moderately strong. Aspect: About 35° from vertical. Texture and luster: Initially, sparsely pubescent and becoming smooth and glabrous with development; glossy. Color, developing: Close to 146C. Color, developed: Close to 146A.

*Leaves*.—Arrangement: Alternate, simple. Length: About 14.9 cm. Width: About 11.8 cm. Shape: Ovate, asymmetrical. Apex: Acute. Base: Truncate with cordate tendencies. Margin: Crenate to dentate; undulate. Texture and luster, upper surface: Smooth, glabrous; slightly velvety; slightly glossy. Texture and luster, lower surface: Sparsely pubescent along venation; slightly glossy. Venation pattern: Laciniate. Color: Developing leaves, upper surface: Close to 143A. Developing leaves, lower surface: Close to between 146C and 147C. Fully expanded leaves, upper surface: Darker than between 147A and N189A; venation, close to 143A. Fully expanded leaves, lower surface: Close to 147B strongly tinged with close to 183C to 183D; venation, close to 146B. Petioles: Length: About 8.3 cm. Diameter: About 5 mm. Strength: Low, flexible. Texture and luster, upper and lower surfaces: Sparsely pubescent; moderately glossy. Color, upper surface: Close to 152A; distally, close to 181B. Color, lower surface: Close to 152A. Stipules: Length: About 1.2 cm. Width: About 1.3 cm. Shape: Deltoid to broadly ovate. Apex: Bluntly acute. Base: Broadly cuneate. Margin: Finely ciliate. Texture and luster, upper and lower surfaces: Smooth, glabrous; moderately glossy. Color, upper and lower surfaces: Close to 144D; apex, tinged with close to 180C.

Flower description:

*Flower appearance and flowering habit*.—Semi-double type rotate flowers with four tepals and numerous tepaloids; flowers arranged in axillary compound cymes; freely flowering habit with typically about seven flowers per cyme and about 140 flowers and flower buds developing per plant; many cymes in flower simultaneously; flowers positioned above and beyond the foliar plane and face upright to outwardly; only male flower development has been observed to date.

*Natural flowering season*.—Plants begin flowering about five weeks after planting; plants will flower year round regardless of nyctoperiod, however plants flower earlier and more abundantly from spring into the autumn in The Netherlands.

*Postproduction longevity*.—Individual flowers last about ten days on the plant; flowers not persistent; excellent postproduction longevity, plants maintain good substance for about five to six weeks in an interior environment.

*Fragrance*.—None detected.

*Inflorescence height*.—About 20.3 cm.

*Inflorescence diameter*.—About 12.5 cm.

*Flowers*.—Shape: Rotate, semi-double type. Diameter: About 6.3 cm. Depth (height): About 1.5 cm.

*Flower buds*.—Length: About 1.9 cm. Diameter: About 0.8 cm to 1.6 cm. Shape: Broadly ovate, flattened.

Texture and luster: Glabrous; slightly velvety; slightly glossy. Color: Close to 48B.

*Tepals*.—Quantity and arrangement per flower: Usually about four per flower arranged in two whorls. Length, lower tepals: About 3.3 cm. Width, lower tepals: About 4 cm. Length, upper tepals: About 3.3 cm. Width, upper tepals: About 3.6 cm. Shape, all tepals: Reniform. Apex, all tepals: Rounded. Base, all tepals: Reniform. Margin, all tepals: Entire; slightly undulate. Texture and luster, upper surface, lower tepals: Smooth, glabrous; moderately velvety; matte. Texture and luster, lower surface, lower tepals: Smooth, glabrous; moderately velvety; slightly glossy. Texture and luster, upper and lower surfaces, upper tepals: Smooth, glabrous; moderately velvety; matte. Color, lower tepals: When opening, upper surface: Close to 31C to 31D; fading towards the margins to close to 43D. When opening, lower surface: Close to 174D; fading towards the margins to close to 37A and 39B. Fully opened, upper surface: Close to 22B; fading towards the margins to close to 48D; venation, similar to lamina color; colors do not change with development. Fully opened, lower surface: Close to 22B; fading towards the margins to close to 48C to 48D; venation, close to 26B; colors do not change with development. Color, upper tepals: When opening, upper surface: Close to 29A to 29B. When opening, lower surface: Close to 49A. Fully opened, upper surface: Close to 20A; fading towards the margins to close to 37C; venation, similar to lamina color; colors do not change with development. Fully opened, lower surface: Close to 20A; fading towards the margins to close to 49D; venation, close to 26B; colors do not change with development.

*Tepaloids*.—Quantity and arrangement per flower: Typically about 35 per flower clustered at the center of the flower. Length: About 0.9 cm to 2.2 cm. Width: About 0.5 cm to 1.6 cm. Shape: Obovate. Apex: Rounded to shallowly cleft. Base: Attenuate. Margin: Entire; slightly undulate. Texture and luster, upper surface: Smooth, glabrous; moderately velvety; matte. Texture and luster, upper surface: Smooth, glabrous; slightly velvety; matte. Color: When opening, upper surface: Close to 29A; towards the base, tinged with close to 13A. When opening, lower surface: Close to 38A; towards the base, close to 20A. Fully opened, upper surface: Close to 29C; fading towards the base to close to 13A; inner tepaloids, close to 14B; venation, similar to lamina color; color does not change with development. Fully opened, lower surface: Close to 37C; fading towards the base to close to 15B; inner tepaloids, close to 14B; venation, close to 26B; color does not change with development.

*Peduncles*.—Length: About 16.1 cm. Diameter: About 5 mm to 6 mm. Strength: Moderately strong. Aspect: About 35° from lateral branch axis. Texture and luster: Moderately pubescent; moderately glossy. Color: Close to 146B.

*Pedicels*.—Length: About 3.4 cm. Diameter: About 2.5 mm. Strength: Moderately strong. Aspect: About 30° from peduncle axis. Texture and luster: Smooth, glabrous; glossy. Color: Close to between 152A and 199A.

*Flower bracts*.—Quantity per flower: Two. Length: About 1.7 cm. Width: About 1.4 cm. Shape: Broadly ovate. Apex: Bluntly acute. Base: Broadly cuneate. Margin: Finely ciliate. Texture and luster, upper and lower surfaces: Smooth, glabrous; slightly glossy. Color, upper and lower surfaces: Close to 144B; apex tinged with close to 180A; venation, similar to lamina color.

*Reproductive organs*.—Stamens: Quantity per flower: About 16, mostly deformed. Filament length: About 5 mm. Filament color: Close to 12A. Anther length: About 4 mm. Anther diameter: About 1 mm to 2 mm. Anther shape: Obovate, flattened. Anther color: Close to 14B. Pollen amount: None observed to date. Pistils: None observed; female flower development has not been observed on plants of the new *Begonia* to date; no seed nor fruit production has been observed to date.

Disease & pest resistance: Resistance to pathogens and pests common to *Begonia* plants has not been observed on plants of the new *Begonia* to date.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'KRBEVPE02' as illustrated and described.

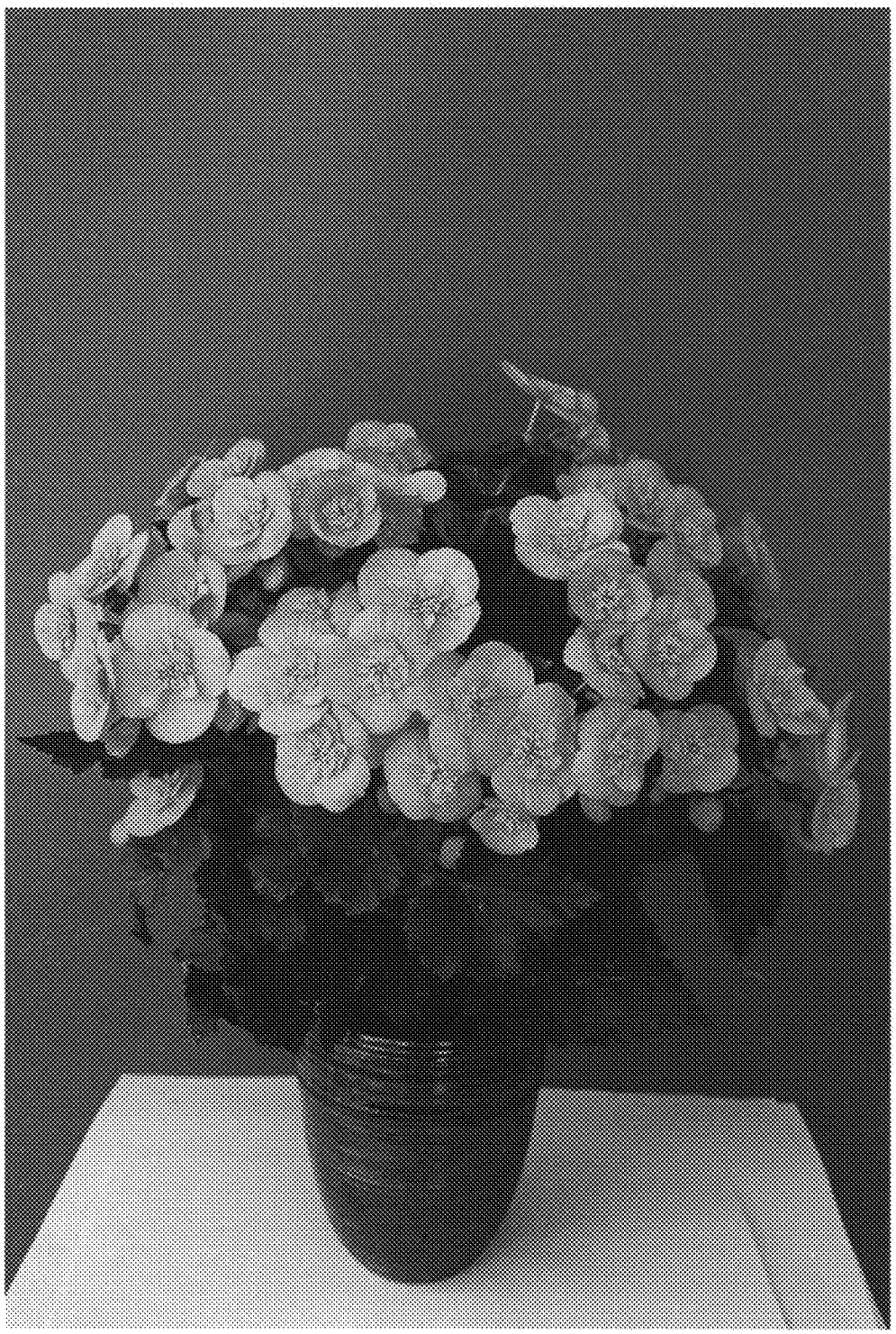

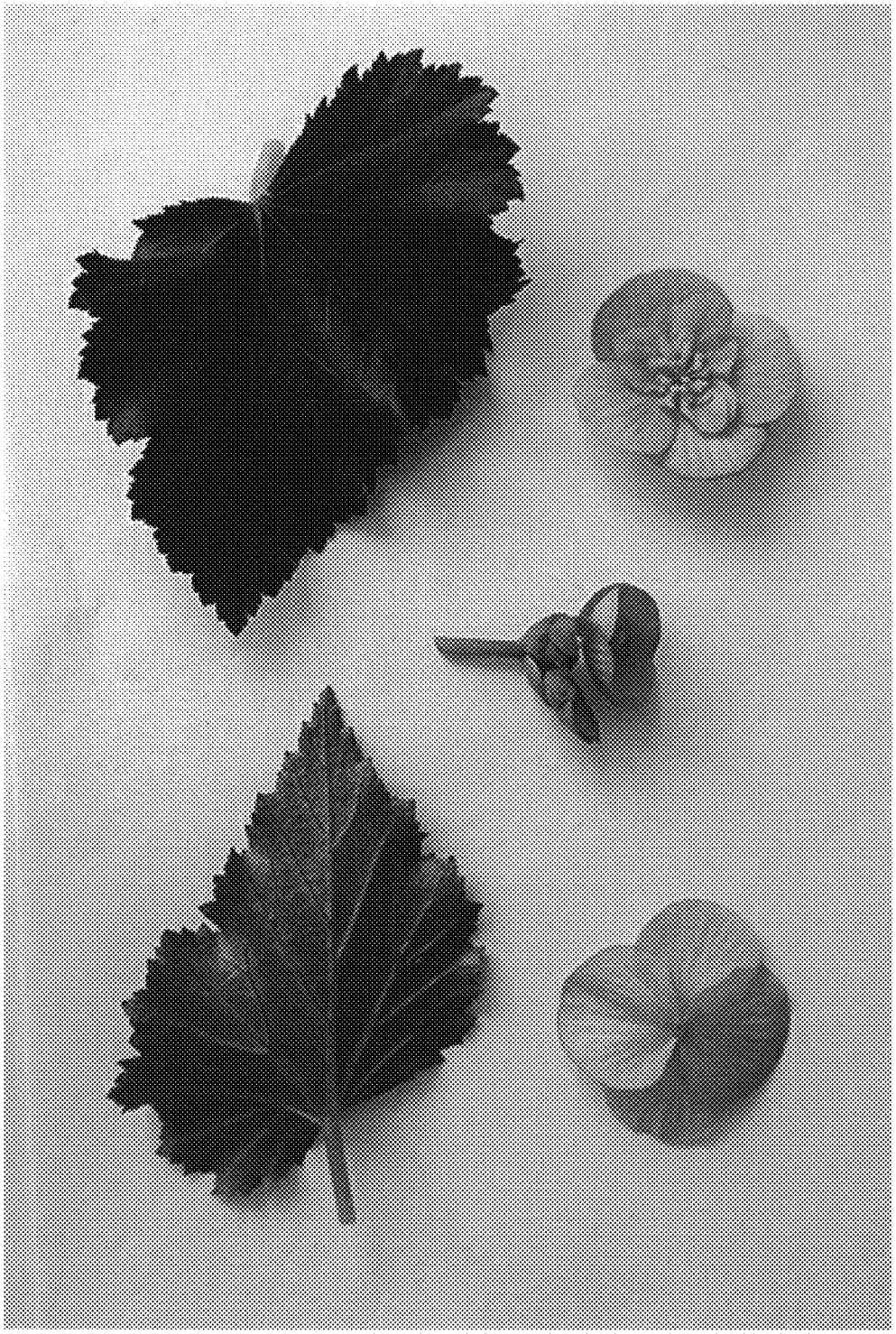

* * * * *